United States Patent [19]

Velenyi et al.

[11] 4,293,719

[45] Oct. 6, 1981

[54] MANUFACTURE OF HYDROPEROXIDES

[75] Inventors: Louis J. Velenyi, Lyndhurst; Serge R. Dolhyj, Parma; Marcia H. Sundeen, Cleveland Hts., all of Ohio

[73] Assignee: The Standard Oil Company, Cleveland, Ohio

[21] Appl. No.: 135,306

[22] Filed: Mar. 31, 1980

[51] Int. Cl.$^3$ .......................................... C07C 179/035
[52] U.S. Cl. .................................... 568/573; 568/565; 568/577
[58] Field of Search ................ 568/573, 577, 565, 569

[56] References Cited

U.S. PATENT DOCUMENTS

| | | | |
|---|---|---|---|
| 3,160,668 | 12/1964 | Davies | 568/573 |
| 3,873,625 | 3/1975 | Barone | 568/573 |
| 4,028,428 | 6/1977 | Brownstein et al. | 568/575 |
| 4,034,047 | 6/1977 | Angstadt | 568/575 |

*Primary Examiner*—Werren B. Lone
*Attorney, Agent, or Firm*—Gary R. Plotecher; Herbert D. Knudsen; Larry W. Evans

[57] ABSTRACT

Hydroperoxides, such as cyclohexylbenzene hydroperoxide, are manufactured by the oxidation of aryl compounds, such as cyclohexylbenzene, in the presence of a catalyst selected from the group consisting of $C_6$–$C_{18}$ primary amines and polyvinylpyrrolidone.

12 Claims, No Drawings

MANUFACTURE OF HYDROPEROXIDES

BACKGROUND OF THE INVENTION

1. Field of the Invention

This invention relates to catalysis. In one aspect, the invention relates to the catalytic manufacture of aryl hydroperoxides from corresponding aryl compounds while in another aspect, the invention relates to specific catalysts useful in this manufacture.

2. Description of the Prior Art

The oxidation of aryl compounds to form aryl hydroperoxides is known generally. For example, the first step in a widely practiced process for manufacturing phenol is the oxidation of cumene to cumene hydroperoxide and was first demonstrated by Hock and Lang, Chem. Ber., 77B, 257, in 1944. Since that time many improvements have been made as illustrated by U.S. Pat. No. 2,547,938 (use of base, emulsifying agent and initiator), U.S. Pat. No. 2,973,310 (use of hydrogen bromide or a bromene salt as a catalyst), U.S. Pat. No. 3,290,384 (use of alkali or alkaline earth metal salt of an oxy acid of plumbate, bismuthate, stannate or antimonate), U.S. Pat. No. 3,959,381 (using cumene hydroperoxide as an initiator), U.S. Pat. No. 4,022,841 (using organometallic complexes as catalyst), and U.S. Pat. No. 4,034,047 (using polyacrylonitrile as a catalyst).

As is evident from the preceding, much of the past research effort has been directed to the identification and development of useful hydroperoxidative catalysts. However, many prior art catalysts are not truly catalysts but are merely vehicles which provide favorable conditions for a hydroperoxidative reaction. For example, the addition of base to the reaction mixture removes the organic acids formed during reaction which, if allowed to remain, would decompose the hydroperoxidation products resulting in unwanted by-products. As another example, emulsifiers merely increase the surface area between the gaseous oxygen and the liquid aryl hydrocarbon reactant. Other examples can be cited. As a consequence, the class of materials that are effective hydroperoxidative catalyst is not extensive and is limited generally to phthalocyanines (U.S. Pat. No. 3,873,625), organometallic compounds (U.S. Pat. No. 3,290,384), inorganic compounds (zinc oxide, lead oxide, magnesium oxide, etc.) and certain polymers (U.S. Pat. No. 4,034,047).

SUMMARY OF THE INVENTION

According to this invention, the class of catalysts useful for the hydroperoxidation of aryl compounds to aryl hydroperoxides are now expanded to include catalysts selected from the group consisting of primary amines and polyvinylpyrrolidones. These new catalysts demonstrate both good activity and excellent selectivity to the desired product. Moreover, the class of aryl compounds which can be hydroperoxidized by these new catalysts include cycloaliphatic-substituted aryl compounds, such as cyclohexylbenzene.

DETAILED DESCRIPTION OF THE INVENTION

Catalyst

Primary amines that can be employed in the practice of this invention are aliphatic amines of 6 to about 18, preferably about 14 to 18, carbon atoms. Although these amines can be either saturated or unsaturated, straight-chained or branched, and unsubstituted or inertly-substituted, they are typically and preferably unsubstituted, straight-chained alkyl amines. By "inertly-substituted" (and like terms) is meant that the one or more substituents on the amine is essentially nonreactive toward the reactants catalyst and products of the reaction under reaction conditions. Although the amines can contain more than one functional amine group, typically the catalyst of this invention contain but one amine functionality. Exemplary amines include hexadecylamine, octadecylamine, dodecylamine, and the like. 1-hexadecylamine is a preferred primary amine.

The polyvinylpyrrolidones that can be used in this invention are known polymers (Kink-Othmer, Encyclopedia of Chemical Technology, 17, 405, 1967) prepared by the addition polymerization of N-vinyl-2-pyrrolidone. Polymers here used are available commercially and range in weight average molecular weight of about 1,000 to about 500,000, with those in the range of about 10,000 to about 100,000 preferred. Depending upon the reaction conditions and molecular weight of the polymer, the polyvinylpyrrolidone catalysts can be either homogeneous (solubilized) or heterogeneous (partially or essentially completely unsolubilized).

Reagents

Aryl hydroperoxides of the formula

are the products of this invention made by contacting a corresponding aryl compound of the formula

where
Ar is an aryl radical, 1 each R is independently hydrogen or a radical of the formula

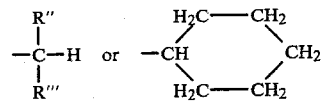

and R' is a radical of the formula

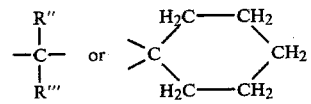

R" and R''' are independently hydrogen or alkyl radicals of 1 to 3 carbon atoms with the proviso that both cannot simultaneously be hydrogen,
m is 1 or 2 with the provisoes that when m is 1, R is not hydrogen, and when m is 2, at least one R is not hydrogen, and
n is 1 or 2.

Representatives compounds of formula II include ethylbenzene, cumene, cyclohexylbenzene, bicyclohexylbenzene, diisopropylbenzene, 2-phenylbutane, 3-phenylhexane, p-cyclohexylisopropylbenzene and the like. The representative hydroperoxides of I include ethylbenzene hydroperoxide, cumene hydroperoxide, cyclohexylbenzene hydroperoxide, bicyclohexylbenzene dihydroperoxide, 2-phenylbutane hydroperoxide, 3-phenylhexane hydroperoxide and the like. This invention is particularly useful for the production of cumene hydroperoxide from cumene and cyclohexylbenzene hydroperoxide from cyclohexylbenzene, these reactions graphically depicted as III and IV respectively.

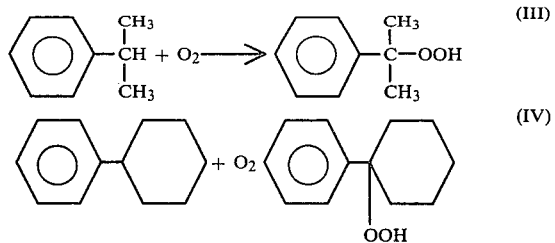

The oxygen required in this invention is typically employed as molecular oxygen. Either pure or diluted oxygen can be used with air being the most typical and convenient form and source of the oxygen employed.

Process Conditions

Hydroperoxidative conditions are here used. These conditions are defined as those at which the compounds of II can be oxidized with molecular oxygen to the compounds of I in the presence of either the primary amines or polyvinylpyrrolidone previously described. Typically, the temperature ranges from approximately 90° to about 130° C. and preferably about 100° to about 120° C. Temperatures less than about 90° C. and greater than about 130° C. can be employed but usually to no advantage.

Atmospheric, subatmospheric or superatmospheric pressure can be employed, the exact amount critical only in its relationship to temperature and usually determined by matters of convenience and economy. Pressures in excess of atmospheric pressure, typically up to about 25 atmospheres, are preferred since such pressures favor hydroperoxide formation and thus tend to enhance product yield.

While the reaction time can vary widely, the longer the reaction mixture is held at elevated temperatures, the more product can decompose. Accordingly, preferably the reaction is conducted only for a sufficient time to reach optimum hydroperoxide yield and then terminated. The reaction time of about 180 minutes is a typical minimum while the reaction time of about one day is a typical maximum. Optimum times are dependent upon many variables including the nature and form of the reagents and catalysts, temperature, etc.

Solvents are necessary to the practices of this invention only to the extent that the starting material is a solid at reaction conditions. If the aryl compounds are liquid at such conditions, then the reaction can be conducted neat. If a solvent is employed, then it is one that is essentially inert to the reaction reagents, catalyst and products at reaction conditions and typical such solvents include the various aliphatic hydrocarbons, chlorinated aromatics, halogenated hydrocarbons and the like. These solvents are liquid at reaction conditions and preferably have a boiling point in excess of the operating temperature of the reaction. n-Heptane, toluene, n-octane, chlorobenzene, p-xylene and pyridine are all examples of suitable solvents.

Like the other reaction parameters, the relative amounts of reagents and catalysts employed in this invention are not critical. Obviously, the reaction requires stoichiometric amounts of aryl compound and oxygen, the exact amounts dependent upon the number of hydroperoxizable sites on the aryl compounds (when n is 1, the ratio of II to oxygen is 1 and when n is 2, the ratio of II to oxygen is 1:2). From the perspectives of economy and convenience, the reaction is performed in an excess of oxygen.

Sufficient primary amine or polyvinylpyrrolidone to catalyze the reaction is employed. Typically, this amount is at least about 0.05 weight percent, based upon the weight of the aryl compound, and preferably at least about 1 weight percent. While amounts in excess of 10 weight percent can be employed, such amounts usually afford no advantage to the invention.

Other compounds that can be present in the reaction mixture include bases, emulsifiers and initiators. Bases, such as hydroxides and carbonates, are useful for maintaining a state of alkalinity which in turn suppress the formation of unwanted by-products. Emulsifiers enhance the surface area between the aryl compound and molecular oxygen thus providing a more efficient reaction. Initiators, such as alkyl- and cycloalkyl-substituted aryl hydroperoxide, can be employed to enhance the rate of reaction or in other words, in reducing the incubation time needed to form enough hydroperoxide to accelerate the rate of reaction to a practical point. Preferably, the initiator is the same as the desired hydroperoxidation product, e.g. in cumene hydroperoxidation, cumene hydroperoxide is the initiator. In commercial applications, part of the product can be recycled for this purpose.

Product

The products of this invention are made by the hydroperoxidation of the corresponding aryl compound, e.g. cumene hydroperoxide is made from the peroxidation of cumene cyclohexylbenzene hydroperoxide is made from the peroxidation of cyclohexylbenzene, etc. Hydroperoxidation will occur at the secondary or tertiary carbon adjoining the aromatic nucleus and if the aromatic compound has more than 1 such carbon, then hydroperoxidation will occur at both such carbons. The products are useful intermediates in the production of phenol and dihydroxybenzene, both manufactured by the acid cleavage of the hydroperoxidative product. For example, the acid cleavage of cumene hydroperoxide forms phenol and acetone while the acid cleavage of cyclohexylbenzene hydroperoxide forms phenols and cyclohexanone.

The following examples are illustrative of certain embodiments of this invention. Unless indicated to the contrary, all parts and percentages are by weight.

SPECIFIC EMBODIMENTS

Procedure

Examples 1–7 and controls A–L were performed at atmospheric pressure with cyclohexylbenzene as the aryl compound and molecular oxygen as the peroxidation agent. Cumene hydroperoxide was used as an initiator in each run. Some runs employed n-octane as a solvent, others toluene and yet others were performed neat. 50 grams of cyclohexylbenzene, 0.5 grams of catalyst and 0.5 grams of initiator were used. The catalyst, cyclohexylbenzene, cumene hydroperoxide and optionally the solvent were placed in a round-bottom 3-neck flask fitted with a condenser, thermometer and a stainless steel oxygen inlet tube. The flask was heated on a heating mantel with continuous stirring while the oxygen was sparged through the liquid at a typical flow rate of about 90 cc/min. Samples were taken periodically and titrated with sodium thiosulfate to determine the percentage of cyclohexylbenzene hydroperoxide formed. The experiments were conducted at 115° C. and the results with various catalysts, both within and without this invention, are reported in Table I.

TABLE I

HYDROPEROXIDATION OF CYCLOHEXYLBENZENE TO CYCLOHEXYLBENZENE HYDROPEROXIDE

| Example | Catalyst | Solvent | Conversion of CBX to CBXHOP[1] | Reaction Time |
|---|---|---|---|---|
| 1 | PVP[2] | n-Octane | 23.3 | 24 hrs |
| 2 | 1-Octadecylamine | " | 12.2 | " |
| 3 | 1-Octadecylamine | " | 3.6 | 4.5 hrs |
| 4 | 1-Hexadecylamine | — | 4.4 | " |
| 5 | 1-Dodecylamine | — | 2.9 | " |
| 6 | 1-Octylamine | — | 3.0 | " |
| 7 | 1-Hexylamine | — | 2.8 | " |
| Control | | | | |
| A | PVP/PS[3] | n-Octane | 5.1 | 24 hrs |
| B | PBA[4] | " | 1.7 | " |
| C | Diethylene Triamine | Toluene | 0 | " |
| D | Tributylamine | " | 0 | " |
| E | Stearamide | " | 6.7 | " |
| F | Piperazine | n-Octane | 0 | " |
| G | Butylamine | — | 0.6 | 4.5 hrs |
| H | Dibenzylamine | — | 0.3 | " |
| I | Melamine | n-Octane | 5.7 | 24 hrs |
| J | N-Benzylidene Methylamine | " | 1.8 | " |
| K | Phenylene Diamine | " | 0 | " |
| L | Dicyclohexylamine | " | 0 | " |

[1] Conversion = $\frac{\text{Cyclohexylbenzene hydroperoxide product} \times 100}{\text{Cyclohexylbenzene reacted}}$
[2] Poly(vinyl)pyrrolidone of about 40,000 weight average molecular weight.
[3] Poly(vinyl)pyridine/polystyrene
[4] Polybenzylamine As is evidenced by these tabulated results, this invention shows good effectiveness for the production of aryl hydroperoxide as compared to processes employing materials as catalysts not within the scope of this invention.

EXAMPLES 8 and 9

The procedure of Examples 1–7 and Controls A–L was repeated except cumene was substituted for cyclohexylbenzene, superatmospheric pressure was substituted for atmospheric pressure, and no solvent was used. The catalysts and results are reported in Table II.

TABLE II

HYDROPEROXIDATION OF CUMENE TO CUMENE HYDROPEROXIDE

| Example | Catalyst | Pressure (psig) | Conversion[1] | Reaction Time |
|---|---|---|---|---|
| 8 | PVP[2] | 200 | 20.2 | 4.25 hrs |
| 9 | 1-Hexyldecylamine | 280 | 20.5 | 3.5 hrs |

[1] Conversion = $\frac{\text{Cyclohexylbenzene hydroperoxide product} \times 100}{\text{Cyclohexylbenzene reacted}}$
[2] Poly(vinyl)pyrrolidone of about 40,000 weight average molecular weight.

Although the invention has been described in considerable detail through the preceding examples and controls, this detail is for the purpose of illustration only and it is not to be construed as a limitation upon the spirit and scope of the following claims.

The claimed invention is:

1. A process for manufacturing an aryl hydroperoxide of the formula $$Ar-(R'-OOH)_n \quad (I)$$

from a corresponding aryl compound of the formula $$Ar-(R)_m \quad (II)$$

where
Ar is an aryl radical, each R is independently hydrogen or a radical of the formula

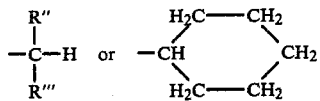

each R' is a radical of the formula

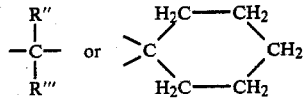

R" and R'" are independently hydrogen or alkyl radicals of 1 to 3 carbon atoms with the proviso that both cannot be simultaneously hydrogen, m is 1 or 2 with the provisoes that when m is 1, R is not hydrogen, and when m is 2, at least one R is not hydrogen, and n is 1 or 2, the process comprising contacting (II) with molecular oxygen at hydroperoxidative conditions in the presence of an initiator and a catalyst selected from the group consisting of $C_{14}$-$C_{16}$ straight-chain, primary alkyl amines amine and poly(vinyl)pyrrolidone having a weight average molecular weight of at least about 1,000.

2. The process of claim 1 where the poly(vinyl)pyrrolidone has a weight average molecular weight between about 10,000 and 100,000.

3. The process of claim 2 where R″ and R‴ are methyl radicals.

4. The process of claim 3 where the temperature ranges from approximately 90° to 130° C.

5. The process of claim 4 where the pressure is atmospheric or superatmospheric.

6. The process of claim 5 where the catalyst is present in at least about 0.05 weight percent based upon the weight of the aryl compound of formula II.

7. The process of claim 6 where the aryl compound of formula II is cumene or cyclohexylbenzene.

8. The process of claim 7 where the catalyst is 1-hexadecylamine or poly(vinyl)pyrrolidone having a weight average molecular weight of about 40,000.

9. The process of claim 8 where the aryl compound of formula II is cumene and the initiator is cumene hydroperoxide.

10. The process of claim 1 where the initiator is an alkyl- or cycloalkyl-substituted aryl hydroperoxide.

11. The process of claim 1 where the initiator is an aryl hydroperoxide of formula I.

12. The process of claim 1 where the Ar of formulae I and II is phenyl.

* * * * *